United States Patent [19]
Zemel

[11] Patent Number: 4,644,380
[45] Date of Patent: Feb. 17, 1987

[54] SUBSTANCE-SENSITIVE ELECTRICAL STRUCTURES

[75] Inventor: Jay N. Zemel, Jenkintown, Pa.

[73] Assignee: University of Pennsylvania, Philadelphia, Pa.

[21] Appl. No.: 288,378

[22] Filed: Jul. 30, 1981

Related U.S. Application Data

[62] Division of Ser. No. 858,906, Dec. 8, 1977, Pat. No. 4,302,530.

[51] Int. Cl.[4] .................... H01L 29/78; H01L 49/00; G01N 27/40; G01N 27/22
[52] U.S. Cl. ...................... 357/25; 204/418; 333/99 R; 333/236; 361/280; 357/23.15; 357/72
[58] Field of Search ............ 204/418; 357/25, 52, 357/54, 72, 23.15; 333/99 R, 236; 361/280, 286

[56] References Cited

U.S. PATENT DOCUMENTS

| | | | |
|---|---|---|---|
| 3,373,323 | 3/1968 | Wolfrum et al. | 357/14 |
| 3,753,720 | 8/1973 | Klozewski et al. | 357/72 |
| 3,831,432 | 8/1974 | Cox | 357/25 |
| 3,953,877 | 4/1976 | Sigusch et al. | 357/72 |
| 3,966,580 | 6/1976 | Janata et al. | 204/195 B |
| 3,999,122 | 12/1976 | Winstel et al. | 357/23 I |
| 4,020,830 | 5/1977 | Johnson et al. | 357/25 |
| 4,103,227 | 7/1978 | Zemel | 324/71.5 |
| 4,158,807 | 6/1979 | Senturia | 357/25 |
| 4,180,771 | 12/1979 | Guckel | 357/25 |
| 4,571,543 | 2/1986 | Raymond et al. | 357/25 |

FOREIGN PATENT DOCUMENTS 2096825  10/1982  United Kingdom ................ 357/25

OTHER PUBLICATIONS

Bergveld, IEEE Trans. on Biomedical Engineering, vol. BME 19, No. 5, Sep. 1972, pp. 342–351 (particularly p. 345).

Janata et al., "Chemically Sensitive Field Effect Transistors", Biomedical Engineering, Jul. 1976, pp. 241–245.

Moss et al., "Potassium Ion Sensitive Field Effect Transistor", Analytical Chemistry, 47, No. 13, Nov. 1975.

Primary Examiner—William D. Larkins
Attorney, Agent, or Firm—Stevens, Davis, Miller & Mosher

[57] ABSTRACT

Disclosed is a substance-sensitive semiconductor and a method for making the same, wherein a substance-sensitive material is combined with photoresist material and applied to an electronic device structure. The substance-sensitive material may be applied before or after the photoresist material, or even may be combined with the photoresist material to form a substance-sensitive layer of photoresist material on the semi-conductor. The photoresist material is then processed, such that unwanted, or undesirable areas are free from the photoresist material and the areas of desired substance sensitivity have a fully processed photoresist layer. A further embodiment of the present disclosure provides multiple layers sensitive to different ions on a single sheet of semiconductor or electromagnetically active material.

20 Claims, 12 Drawing Figures

SUBSTANCE-SENSITIVE ELECTRICAL STRUCTURES

This is a division, of application Ser. No. 858,906, filed Dec. 8, 1977, now U.S. Pat. No. 4,302,530,

BACKGROUND OF THE INVENTION

The present invention relates generally to electronic and electromagnetic devices for the determination of the presence and strength of selected substances which include ions, molecules and ligands.

Often times it is advantageous to detect the existence and/or concentration of substances in the atmosphere or solutions. Generally such detectors involved exposure of a chemical compound to the test medium with the indication of existence and/or concentration being provided by a color change, the formation of a precipitate, etc.

In the recent past, however, it has become possible to provide semiconductors which are sensitive to the exsistence of specific substances in liquids or gases, and provide an electrical indication of both the presence and concentration therein. Examples of these are the ion-sensitive field effect transistor (ISFET), one example of which is shown in U.S. Pat. No. 3,831,432, and the ion controlled diode disclosed in co-pending U.S. patent application Ser. No. 781,474, filed Mar. 25, 1977, herein incorporated by reference. Both devices incorporate an ion sensitive membrane which forms a charge layer near the semiconductor junction which is dependent upon the concentration of the ion, molecule or complex, whose concentration is to be determined. The substance-sensitive material varies widely in its individual makeup dependent upon the particular substance to which the material is sensitive. Many different materials can be used in the membrane construction in order to achieve varied substance-sensitivity. For example, one such substance-sensitive material which is sensitive to potassium ions ($K^+$ ions) is valinomycin. Some other substance-sensitive materials are listed in *Membrane Electrodes* by N. Lakshminarayanaiah, Academic Press, 1976, also herein incorporated by reference.

In the prior art substance-sensitive devices, the substance-sensitive material is formed into a cast membrane which is then located over the semiconductor device. Alternately, the semiconductor device can be coated with the appropriate material. While these methods of forming the substance-sensitive membrane are suitable for a single device capable of providing an electrical indication of the concentration of a single complex, it is extremely difficult to utilize cast membranes, or substance-sensitive coatings, to render only discrete portions of a Large-Scale Integrated (LSI) circuit involving semiconductors, microwave striplines or integrated optical structures sensitive to the substance. Thus, in the common mass production of integrated circuits, it is extremely difficult, if not impossible, to provide appropriate amplifier circuitry along with a substance-sensor in a mass-produced integrated semiconductor, microwave or optical circuit.

The difficulty of obtaining precise placement (measured in microns) of a cast membrane, eliminates the applicability of cast membranes to LSI structures. If existing LSI structures are coated with substance-sensitive materials, it would be possible to detect only one substance, and not a plurality of different substances.

SUMMARY OF THE INVENTION

Therefore, it is an object of the present invention to provide a semiconductor, microwave, or optical device which is sensitive and provides an electrical indication of the existence and/or concentration of a predetermined substance, which device can be produced in accordance with existing mass production techniques.

It is a further object of the present invention to provide a method of forming a substance-sensitive semiconductor, microwave or optical device under current mass production technology.

It is a still further object of the present invention to provide a method of forming substance-sensitive layers on semiconductors, microwave or optical devices which are sensitive to different substances utilizing current mass production technology.

An additional object of the present invention is to provide a substance-sensitive semiconductor having a substance-sensitive photoresist layer which is compatible with large-scale integrated circuit technology.

It is a still further object of the present invention to provide a substance-sensitive semiconductor which incorporates multiple substances-sensitive sensors.

The above, and other objects, are achieved by the method of incorporating substance-sensitive material with photoresist material, and applying the combination to the required portion of a semiconductor. The photoresist material is masked, exposed to radiation, etched and chemically treated to leave a substance-sensitive photoresist layer only on selected portions of the semiconductor material. In preferred embodiments, a plurality of photoresist layers sensitive to differing substances can be provided on adjacent portions of a large scale integrated circuit chip.

BRIEF DESCRIPTION OF THE DRAWINGS

A more complete appreciation of the invention, and the attendant advantages thereof, will be more clearly understood by reference to the following drawings, wherein:

FIGS. 1a-1j are partial, cut-away views of semiconductor material showing the steps utilized in preparing two substance-sensitive membranes, each membrane sensitive to a different substance;

DETAILED DESCRIPTION OF A PREFERRED EMBODIMENT

Figure 1A:
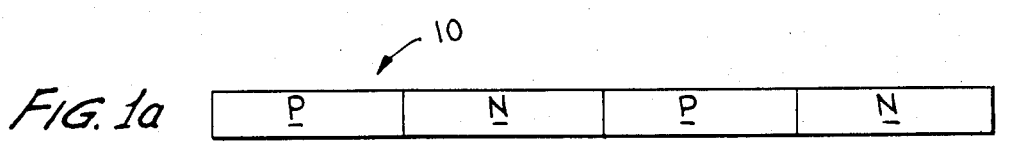
Figure 1B:
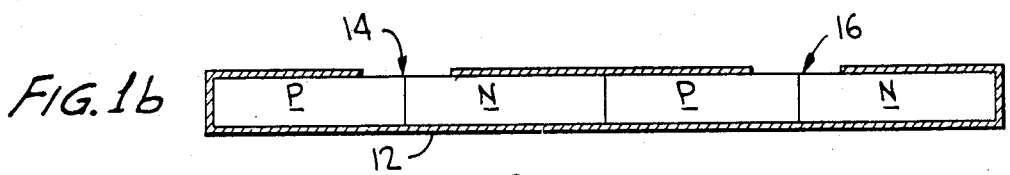
Figure 1C:
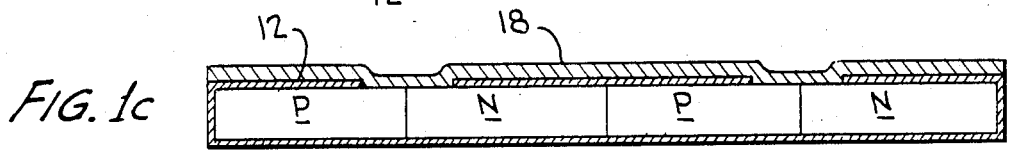
Figure 1D:
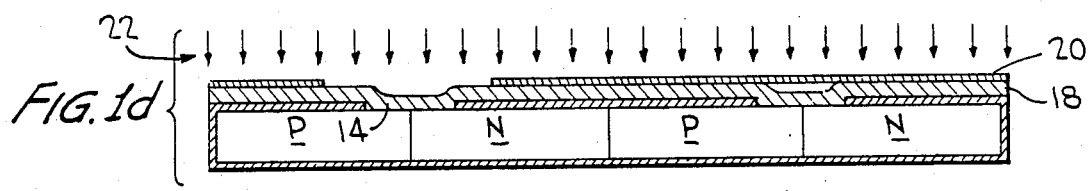
Figure 1E:
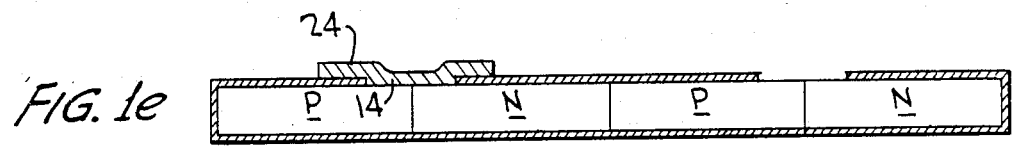
Figure 1F:
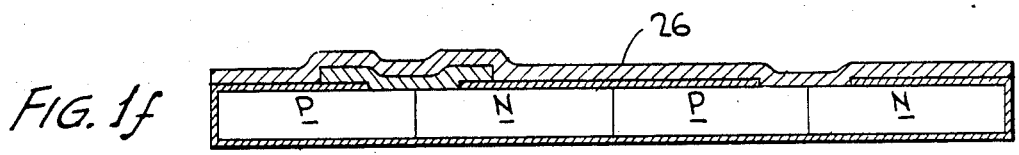

The term photoresist material applies to a large number of commercially available materials which are used in the preparation of semiconductor circuitry. The unique property of photoresist material is that exposure to radiation causes, or prevents, polymerization of the photoresist material, such that the unpolymerized material can be later removed from the device to which the photoresist material, as applied to the present invention, incorporates all materials which are sensitive to radiation exposure (whether it be visible light, ultraviolet, infrared, X-ray, electron beam, ion beam, etc. radiation) when the activation (exposure, or non-exposure) prevents, or causes, a change in the etching rate or polymerization in the material itself. It is this property which enables the present method to achieve the very precise edge definition to substance-sensitive membranes which has theretofore been impossible with cast, or coating, type membranes.

As noted earlier in the Background of the Present Invention, there are a number of materials which are sensitive to the presence and/or concentration of various substances (ions, molecules, ligands and other chemical groups). Because the etching or removal rate of photoresist material changes when activated (by exposure, or non-exposure, to particular radiations depending upon the type of photoresist), small quantities of substance-sensitive materials can be dissolved, and then, fixed in the photoresist material by the activation process. If a photoresist material is doped with a substance-sensitive material, and subsequently activated, the result is a substance-sensitive layer which will remain on the surface of the structure to which the photoresist material is initially applied.

Becuase the combination of photoresist material and substance-sensitive material produces a material whose remaining existence on a surface is dependent upon whether or not it has been exposed to the radiation or not, extremely sharp and precise definition can be given to the edges of photoresist material having the substance-sensitive material suspended therein. Thus, substance-sensitive photoresist layers can be placed on surfaces with an accuracy measured in microns, permitting the application of a plurality of extremely accurate chemical sensors to be produced on a single substrate.

The negative photoresist is activated when exposed to the appropriate radiation, and the positive-type photoresist is activated unless it is exposed to the appropriate radiation.

It is understood that the term "processing" encompasses the steps of selectively activating and removing substance-sensitive photoresist material to leave a substance-sensitive photoresist layer at a designated location, said steps dependent upon the type of photoresist material chosen.

By the same token, layers of substance-sensitive photoresist can be applied to the same substrate, each layer being sensitive to a different type of substance. An example of the inventive method applied to a two substance-sensitive semiconductor is shown in FIGS. 1a–1j.

A semiconductor substrate 10 is shown in FIG. 1a, comprising P-type and N-type semiconductor materials. Because several substance-sensitive elements are going to be placed on the single substrate, a plurality of P/N junctions are provided. A passivation layer 12 is applied to the substrate, with the exception of the prepared places 14 and 16 where the membrane layers are to be placed. The prepared places may include a blocking layer to prevent either electronic or ionic conduction, or mass diffusion, as necessary. The passivation layer may comprise silicon dioxide ($SiO_2$), or any other suitable isolation material known to those in the art.

A first layer of substance-sensitive photoresist material is applied over prepared places 14 and 16, as well as the passivation layer 12. The substance-sensitive photoresist layer can be applied by first coating the passivation layer, and prepared spaces, with a layer of substance-sensitive material, over which is placed a layer of photoresist material, such that the substance-sensitive diffuses into the photoresist layer. Alternatively, a layer of photoresist material can be applied with a coating of substance-sensitive material thereover. The substance-sensitive material is permitted to diffuse into the photoresist material, forming a substance-sensitive photoresist layer. In a preferred embodiment, a substance-sensitive material is first mixed with the photoresist material, and then, applied to the substrate as a substrance-sensitive photoresist layer.

The substrate, covered with the substance-sensitive photoresist layer 18, is covered by a suitable mask 20, and subjected to an appropriate radiation indicated by arrows 22. As is known, photoresist material comprises two primary groups, positive and negative photoresist. In this instance, a negative-type polymerizable photoresist material is depicted, with an appropriate mask 20 to polymerize the substance-sensitive photoresist material in the vicinity of prepared space 14. If a positive-type photoresist material were used, the mask would cover only the vicinity of prepared space 14, allowing the rest of the photoresist material to be exposed to radiation 22, thus, preventing its polymerization.

The unpolymerized substance-sensitive photoresist material is removed by conventional etching procedures, leaving a single substance-sensitive photoresist layer 24 in the region of prepared space 14.

Figure 1G:
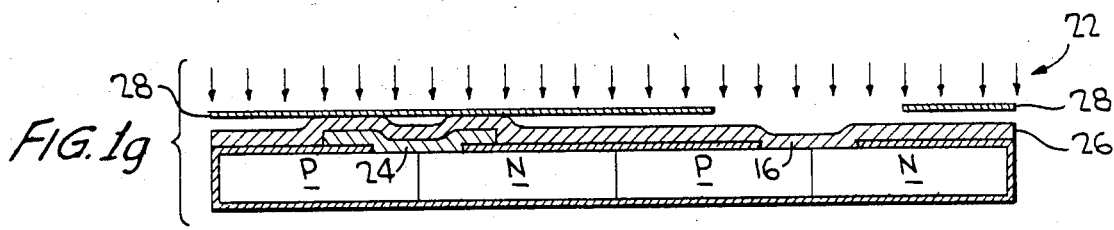
Figure 1H:
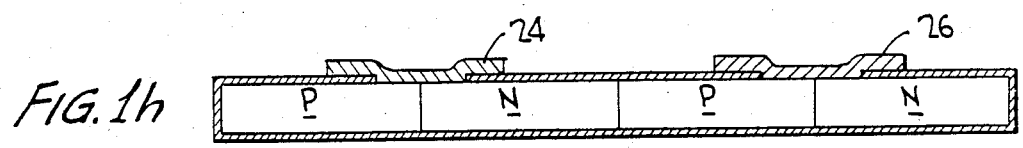
Figure 1I:
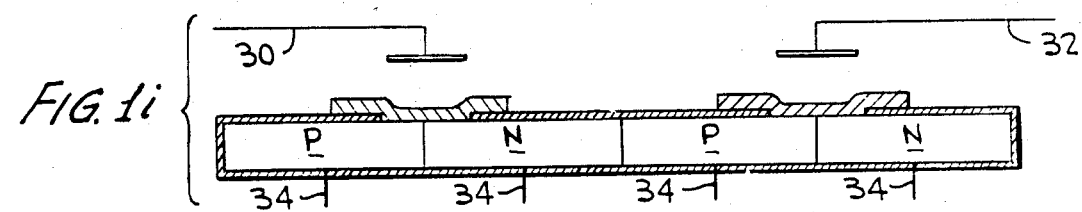

A second layer of substance-sensitive photoresist material 26 is placed over the substrate and isolation layer. However, the second layer of substance-sensitive photoresist may be sensitive to a substance different from that of said first substance-sensitive photoresist layer. As shown in FIG. 1g, a suitable mask 28 is placed over the coated substrate, with arrows 22 indicating the radiation for polymerizing the photoresist layer in the vicinity of prepared space 16. After suitable etching and processing steps, the substrate, as indicated in FIG. 1h, has a substance-sensitive photoresist layers 24 and 26, which are responsive to different substances. After the addition of reference electrodes 30 and 32, and suitable contact electrodes 34, the chemical sensor is ready for operational use, as indicated in FIG. 1j.

It should be noted that, although a multiple substance-sensitive chemical sensor has been shown in FIGS. 1a–1j, the procedure would be precisely the same for making only a single substance-sensitive photoresist layer, or for making a plurality of substance-sensitive sensitive photoresist layers which are sensitive to different substances.

It is clear that many different types of photoresist material, both positive and negative, can be utilized in accordance with the present invention. The process of photopolymerization and the physical and chemical properites of a number of different photoresist materials are further discussed in *Solid State Technology*, June and September, 1971, and *Electronic Components*, June 29, July 27 and August of 1973, said articles herein incorporated by reference. For providing a sustance-sensitive photoresist layer which is sensitive to potassium ($K^+$) ions, valinomycin can be utilized, which is available from Cal-Bio Chem, East Rutherford, New Jersey. One specific photoresist material which was used is type AZ 1350J, available from Shipley, Allentown, Pa. It is clear that many other types of photoresist material, both positive and negative, can be utilized in accordance with the present invention.

Similarly, in order to obtain photoresist layers which are sensitive to different substances, different substance-sensitive material can be utilized as herein before noted. In a preferred embodiment in which the substance-sensitive material is mixed with the photoresist material and then applied to the substrate, 10 mg. of valinomycin was dissolved in 10 cc. of negative photoresist material. The substance-sensitive photoresist material was spun onto a silicon wafer coated with a 6,000 Å thick layer of silicon dioxide, utilizing standard methods. The substance-sensitive photoresist layer was prebaked at a temperature of 50° C. for a short period of time and then exposed to ultraviolet radiation in a standard mask aligner in order to polymerize the materials. Two micron thick and thinner layers of substance-sensitive photoresist material have been provided, which give the necessary sensitivity to the existence, and concentration, of potassium ions.

Figure 4:
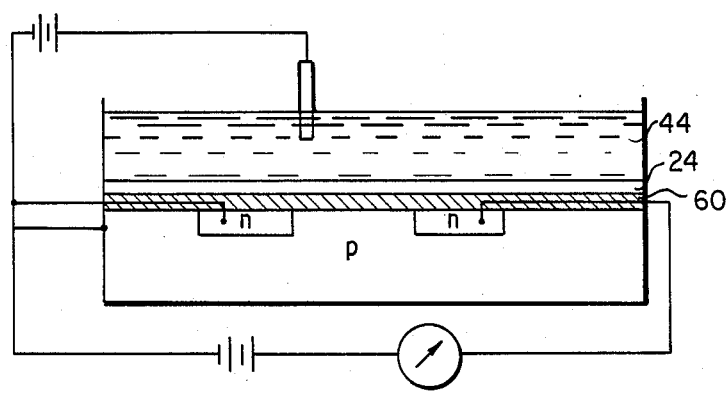
FIG. 4 shows a typical ISFET in which the present invention may be applied.

Instead of providing multiple layers on an ion controlled diode, as represented in FIGS. 1a-1j, the applicants' inventive method could be applied to providing substance-sensitive photoresist layers on ion sensitive field-effect transistors (ISFET) as taught in U.S. Pat. No. 3,831,432. A typical ISFET structure is illustrated in FIG. 4. Although the operation of the semiconductor device is different from that of an ion controlled diode, the effect of the substance-sensitive photoresist layer is similar, and the inventive method can be utilized interchangeably for ion controlled diodes, ISFET's or combinations thereof.

Figure 2:
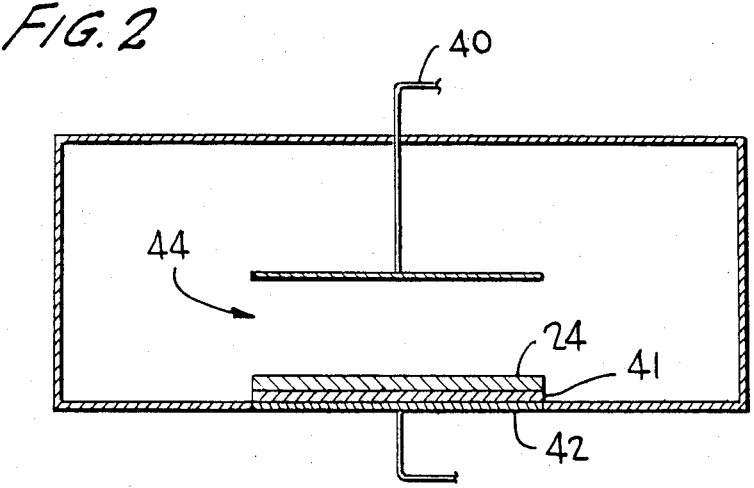
FIG. 2 is a schematic view of a capacitive application of the substance-sensitive layer.

In fact, the inventive method of the present invention can be applied to electronic structures other than semiconductors. FIG. 2 illustrates the utilization of a substance-sensitive photoresist layer to vary the capacitance between the reference electrode 40 and a base electrode 42. The test medium 44 (the material in which it is desired to sense the presence, or concentration, of the desired substance) causes changes in the dielectric constant of the substance-sensitive photoresist layer 24, when the desired substance is present. It is clear that a change in dielectric constant will change the coupling and thus the capacitance between the plates of the capacitor. An isolation layer 41, upon which the photoresist layer is applied, serves to prevent the test medium from shorting the capacitor plates or the photoresist layer. The above is a preferred embodiment, although one could easily locate the photoresist layer on its own isolation layer at any point between the capacitor plates. These changes in the dielectric constant are reflected in changes in capacitance betgween the reference electrode 40 and the base electrode 42. These changes in capacitance can be measured, such that a digital output indicative of the concentration of the unknown complex is provided, as is shown in co-pending application Ser. No. 781,474, filed Mar. 25, 1977.

Figure 3:
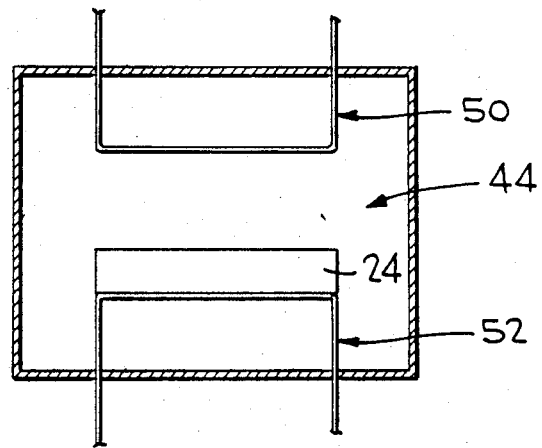
FIG. 3 is a schematic view of an inductive application of the substance-sensitive layer.

Similarly, changes in permittivity and permeability in the substance-sensitive photoresist layer in response to the presence of the desired substance, can be reflected in changes of the coupling between two lines, as is shown in FIG. 3. An input line 50, and an output line 52, are coupled in part by a substance-sensitive photoresist layer 24. Test medium 44 causes changes in the permittivity and permeability of the substance-sensitive photoresist layer, which ultimately causes a change in the coupling between the input line 50 and the output line 52, which change can be measured providing an indication of the concentration of the desired substance. While the FIG. 2 embodiment would have a D.C. or low frequency application, the FIG. 3 embodiment would primarily apply to high frequency devices.

The electronic structures schematically depicted in FIGS. 2 and 3 may be applied to microwave striplines and integrated optical structures, as well as other electronic devices, which will become obvious to those of ordinary skill in the art in view of the above teachings. FIG. 4 illustrates the application of a substance-sensitive layer 24 placed on top of a blocking layer 60 separating a field-effect transistor from test medium 44. Therefore, it is believed that the present inventive method and apparatus is not limited to the specific embodiments herein discussed, and many modifications and variations thereof will be readily apparent to those skilled in the art, in the light of the above teachings. It is, therefore, to be understood that, within the scope of the appended claims, the invention may be practiced otherwise than as specifically described.

The embodiments of the invention in which an exclusive property or privilege is claimed are defined as follows:

1. A substance-sensitive structure for sensing the presence and/or concentration of a substance in a test medium, said structure comprising:
   structure means, responsive to change in a dielectric constant, for indicating the concentration of said substance in said test medium as determined by said change in said dielectric constant; and
   a substance-sensitive layer for separating said structure means from said test medium and for changing dielectric constant in response to the concentration of said substance in said test medium, said layer comprised of substance-sensitive photoresist material including a photoactivator.

2. The structure of claim 5, wherein said structure means comprises a semiconductor diode having a P/N junction with said substance-sensitive photoresist material separating said P/N junction from said test medium.

3. The structure of claim 5, wherein said structure means is a capacitor having at least two plates, and said substance-sensitive photoresist material is disposed between said plates, and said test medium is exposed to said material.

4. A substance-sensitive structure for sensing the presence and/or concentration of a substance in a test medium, said structure comprising:
   structure means, responsive to changes in a dielectric constant, for indicating the concentration of said substance in said test medium indicated by said change in said dielectric constant; and
   a subtance-sensitive layer disposed in said test medium for changing dielectric constant in response to the concentration of said substance, said structure being a pair of lines coupled through said substance-sensitive layer, said layer comprised of substance-sensitive photoresist material.

5. A substance-sensitive structure for sensing the presence and/or concentration of at least a first substance and a second substance in a test medium, said structure comprising:
   a first electronic structure responsive to change in a dielectric constant for indicating the concentration of said first substance in said test medium by said change in said dielectric constant;
   a first substance-sensitive layer for separating said first electronic structure from said test medium and for changing dielectric constant in response to the concentration of said first substance;
   a second electronic structure, integral with said first electronic structure, responsive to change in a dielectric constant for indicating the concentration of said second substance in said test medium by said change in said dielectric constant; and second substance-sensitive for separating said second electronic structure from said test medium and for changing dielectric constant in response to the concentration of said second substance, both of said substance-sensitive layers being comprised of substance-sensitive photoresist material including a photoactivator.

6. The structure of claim 5, wherein said structure means comprises a field effect transistor and said substance-sensitive layer is disposed on said field effect transistor.

7. The structure of claim 6, wherein said field effect transistor comprises:
 a semiconductor substrate;
 a pair of spaced-apart diffusion regions on said semiconductor substrate;
 a blocking layer covering said substrate and spaced-apart diffusion regions;
 a layer of substance-sensitive photo-resist material on said blocking layer; and
 a reference electrode coupled to one of said diffusion regions, said subtance-sensitive layer separating said blocking layer from said test medium and said reference electrode disposed in said test medium.

8. A substance-sensitive structure for sensing the presence and/or concentration of a substance in a test medium, said structure comprising:
 means for changing dielectric constant in response to changes in concentration of said substance in said test medium; and
 means, responsive to changes in said dielectric constant, for indicating the concentration of said substance in said test medium, said indicating means including means for detecting the effect of said changes in dielectric constant on a time varying electrical signal.

9. A substance-sensitive structure for sensing the presence and/or concentration of a substance in a test medium, said structure comprising:
 structure means, responsive to specific changes, for indicating the concentration of said substance in said test medium as determined by said specific changes; and
 a substance-sensitive layer for separating said structure means from said test medium and for specifically changing in response to the concentration of said substance in said test medium, said layer comprised of a photoresist material including a photoactivator and a substance-sensitive material.

10. The structure of claim 9, wherein said structure means comprises a semiconductor diode having a P/N junction with said layer separating said P/N junction from said test medium.

11. The structure of claim 9, wherein said structure means is a capacitor having at least two plates and said layer is disposed between said plates, and said test medium is exposed to said material.

12. A substance-sensitive structure for sensing the presence and/or concentration of a substance in a test medium, said structure comprising:
 structure means, responsive to specific changes, for indicating the concentration of said substance in said test medium indicated by said specific changes; and
 a substnace-sensitive layer disposed in said test medium for specifically changing in response to the concentration of said substance, said structure means being comprised of a pair of lines coupled through said substance-sensitive layer, said layer comprised of a photoresist material including a sensitizer and a substance-sensitive material.

13. The structure of claim 9, wherein said structure means comprises a field-effect transistor and said substance-sensitive layer is disposed on said field-effect transistor.

14. The structure of claim 13, wherein said field-effect transistor comprises:
 a semiconductor substrate;
 a pair of spaced-apart diffusion regions on said semiconductor subtrate;
 a blocking layer covering said substrate and spaced-apart diffusion regions; and
 a reference electrode coupled to one of said diffusion regions, said substance-sensitive layer separating said blocking layer from said test medium and said reference electrode disposed in said test medium.

15. A substance-sensitive structure for sensing the presence and/or concentration of a substance in a test medium, said structure comprising:
 structure means, responsive to a substance-sensitive photoresist layer including a photoactivator, for indicating the concentration of said substance in said test medium as determined by changes in said substance-sensitive photoresist layer; and
 a substance-sensitive photoresist layer for separating said structure means from said test medium and for changing in response to the concentration of said substance in said test medium, said layer further including a substance-sensitive material and said layer further comprising the sole means for bonding said substance-sensitive material to said structure means.

16. The structure of claim 19, wherein said structure means comprises a semiconductor diode having a P/N junction with said substance-sensitive photoresist material separating said P/N junction from said test medium.

17. The structure of claim 19, wherein said structure means is a capacitor having at least two plates and said substance-sensitive photoresist material is disposed between said plates, and said test medium is exposed to said substance-sensitive photoresist material.

18. A substance-sensitive structure for sensing the presence and/or concentration of a substance in a test medium, said structure comprising:
 structure means, responsive to changes in a substance-sensitive photoresist layer, for indicating the concentration of said substance in said test medium; and
 a substance-sensitive layer disposed in said test medium and responsive to the concentration of said substance, said structure means comprising a pair of lines coupled through said substance-sensitive layer, said substance-sensitive layer including a substance-sensitive material and further comprising the sole means for bonding said substance-sensitive material to said structure means.

19. The structure of claim 19, wherein said structure means comprises a field-effect transistor and said substance-sensitive layer is disposed on said field-effect transistor.

20. The structure of claim 23, wherein said field-effect transistor comprises:
 a semiconductor substrate;
 a pair of spaced-apart diffusion regions on said semiconductor substrate;
 a blocking layer covering said substrate and spaced-apart diffusion regions; and
 a reference electrode coupled to one of said diffusion regions, said substance-sensitive layer separating said blocking layer from said test medium and said reference electrode disposed in said test medium.

* * * * *